United States Patent [19]
Loretti et al.

[11] Patent Number: 4,971,765
[45] Date of Patent: Nov. 20, 1990

[54] DEVICE FOR THE SEQUENTIAL TREATMENT OF IMMERSED OBJECTS

[75] Inventors: Maurice Loretti, Chatelaine; Manfred Rocklinger, Carouge, both of Switzerland

[73] Assignees: Essilor International, Creteil Cedex; Galenica Holding SA, Bern, both of Switzerland

[21] Appl. No.: 323,769

[22] Filed: Mar. 15, 1989

[30] Foreign Application Priority Data

Mar. 29, 1988 [CH] Switzerland ............... 1191/88

[51] Int. Cl.[5] ................. A61L 2/18; A61L 2/24
[52] U.S. Cl. ................. 422/116; 422/300; 422/301; 422/61; 206/5.1; 221/86; 141/236; 141/363
[58] Field of Search .......... 422/297, 300, 301, 305, 422/310, 116; 141/236, 284, 363, 364, 365; 221/82, 83, 86; 206/5.1

[56] References Cited

U.S. PATENT DOCUMENTS

| 3,623,492 | 11/1971 | Frantz et al. | 206/5.1 |
| 4,011,941 | 3/1977 | Parsons | 206/5.1 |
| 4,013,410 | 3/1977 | Thomas et al. | 206/5.1 |
| 4,207,992 | 6/1980 | Brown | 221/82 X |
| 4,396,583 | 8/1983 | LeBoeuf | 422/301 |
| 4,798,309 | 1/1989 | Stone et al. | 221/82 X |
| 4,809,877 | 3/1989 | Albright | 221/82 X |
| 4,816,232 | 3/1989 | Barrau et al. | 422/301 |
| 4,826,001 | 5/1989 | Castillo | 422/301 |

Primary Examiner—Robert J. Warden
Assistant Examiner—Jeffrey R. Snay
Attorney, Agent, or Firm—Pollock, VandeSande and Priddy

[57] ABSTRACT

The invention relates to a device for the sequential treatment of immersed objects with dissolved reagents which is particularly suitable for the treatment of contact lenses. The invention further relates to a kit consisting of the above-mentioned device and a container in which unit doses of reagents are stored.

14 Claims, 2 Drawing Sheets

DEVICE FOR THE SEQUENTIAL TREATMENT OF IMMERSED OBJECTS

STATE OF THE ART

Certain objects as delicate as contact lenses require constant care to maintain their properties, for example cleaning, disinfection, decontamination or "deproteinization". To avoid eye irritation, the user cleans his contact lenses daily. Although the manipulations involved are relatively simple, they are still nonetheless delicate since reagents such as oxidizing or acidic products are used, for example hypochlorite, perborate or hydrogen peroxide; the required dosage must be very precise and the reaction time must be measured accurately if deterioration of the lenses is to be prevented.

The order of the operations—decontamination, neutralization, etc.—must of course be respected. Repeated daily, these operations quickly prove tedious and a source of errors, if not accidents; moreover, they occupy the user for more than half an hour, during which period other activities should generally be avoided as they distract the user's attention.

Appropriate apparatuses for making such operations automatic and reliable are not yet available and the user is forced to carry out the above-described manipulations every day, with all the risks this entails. The object of the present invention is to offer the user a simple, safe and effective device which enables the series of operations involved in the treatment of contact lenses to be carried out automatically, respecting the doses of reagents and the reaction times prescribed.

THE INVENTION

The invention achieves the stated object by proposing a device for the sequential treatment of immersed objects with dissolved reagents which comprises the following constituent elements:
- a reservoir for containing the reagent solution,
- a receptacle for keeping the objects to be treated immersed in the reservoir,
- a cover piece fixed to the top of the reservoir, supporting at its center a drive unit coupled to a timer, and having near its periphery an orifice for transferring unit doses of reagents into the reservoir, and
- a mobile dispenser of unit doses of reagents which is centered on the cover piece and bears on the said piece, the said dispenser being designed so as to be rotated by the drive unit, and having near its periphery inlet means for separately bringing each of the unit doses of reagents opposite the orifice in the cover piece.

Some of the characteristics of the device of the invention will become apparent on reading the description. The device defined in this way provides a very advantageous way of overcoming the disadvantages of the techniques hitherto applied to the treatment of soft contact lenses, but its use is obviously not limited to these operations alone. In the treatment of contact lenses in particular, any superfluous contact with the hands and any contamination are avoided as the essential part of the treatment takes place in a closed system.

BRIEF DESCRIPTION OF THE DRAWINGS

The attached drawings illustrate some embodiments of the present invention, solely by way of examples.

PREFERRED EMBODIMENTS OF THE INVENTION

Figure 1:
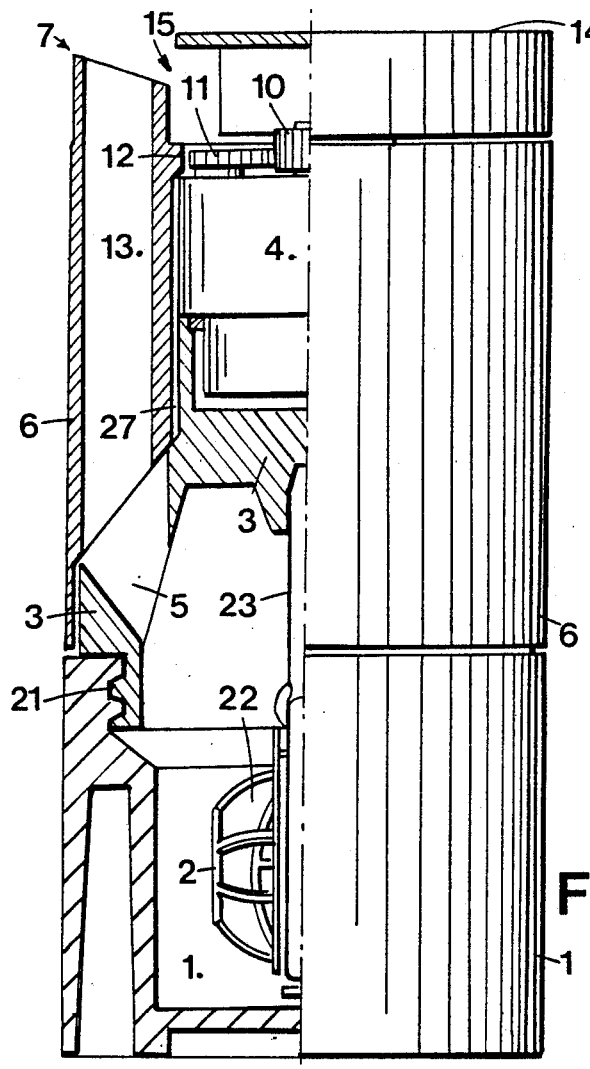
FIG. 1 shows a partial vertical section of a first embodiment of the invention.

In one of the embodiments of the invention, the device takes the following form: it comprises a reservoir 1, of cylindrical general shape and preferably with a flat bottom, which is surmounted by a cover piece 3 fixed to the upper part of the reservoir. The said cover piece 3 can be screwed, for example, to the reservoir 1: in such an embodiment, the periphery of the reservoir has a thread 21 cooperating with the thread provided on the base of the cover piece 3 (FIG. 1). It is of course possible to envisage other fixing systems, for example systems with catches, clips or a ratchet mechanism.

In one particular embodiment of the invention, the useful volume of the reservoir 1 can be minimized. In such a case, its internal diameter will be substantially smaller than the diameter of the base of the device, the said base having the shape illustrated in FIG. 1, for example.

According to the invention, the device also comprises a receptacle 2 located within the reservoir 1 and preferably in its lower part. Thus, once the reservoir has been filled with the appropriate amount of liquid, the objects to be treated can be kept immersed. To favor contact between the objects to be treated and the reagents in solution, the receptacle can have openings 22 or any other suitable open conformation depending in particular on the nature of the objects to be treated. In one of the embodiments of the invention, the receptacle 2 is fixed to the bottom surface of the cover piece 3 by means of a pin 23 (FIG. 1). In such a case, the receptacle remains immobile while the treatment is in progress.

Figure 3:
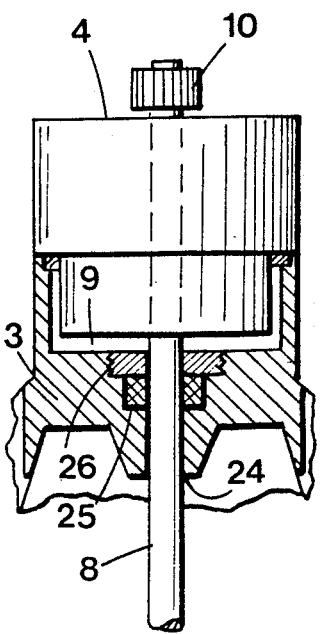
FIG. 3 is a partial vertical section of another embodiment of the invention.

In another embodiment of the invention, the receptacle 2 can be fixed to the spindle 8 of the drive unit 4, which is described in greater detail below. In this embodiment, the spindle 8 passes through a passage 24 created at the center of the piece 3, the seal being provided for example by means of an O-ring 25 held in its seat by a washer 26. The receptacle can thus be driven by the movement communicated to the spindle of the drive unit 4, which makes it possible to activate the mixture of reagents in solution and accordingly favors contact between the objects being treated and the said solution (FIG. 3).

According to the invention, the cover piece 3 supports at its center a drive unit coupled to a timer and has near its periphery an orifice 5 for transferring unit doses of reagents into the reservoir 1. In one particular embodiment of the invention, the piece 3 is frustoconical and has at its center a housing 9 in which the drive unit 4 is immobilized by any known means (glueing, welding, ratchet mechanism, etc.). In such a case, the base of the mobile dispenser 6 obviously has the appropriate shape, preferably the same frustoconical shape: this gives the fixed and mobile elements a relatively extensive contact area, so the pressure exerted by the dispenser 6 is better distributed and the frictional forces are reduced accordingly. The contact area of each of the above-mentioned elements will preferably be smooth: the synthetic polymeric materials which can be used to manufacture them are capable of achieving this. Such an arrangement is illustrated in FIG. 1.

Of course, the frustoconical arrangement described above is not the only one which can be envisaged, and it is possible just as easily to design a plane contact area perpendicular to the axis of the device or, for example, a contact area in the shape of a spherical cap.

Figure 2:
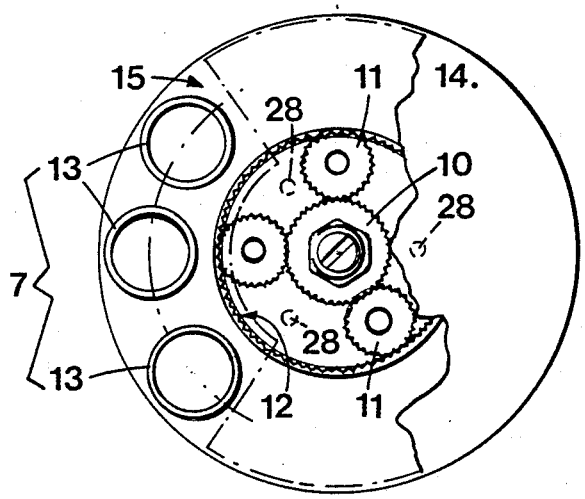
FIG. 2 shows a top view of the embodiment illustrated in FIG. 1.

According to the invention, the drive unit 4 comprises, preferably at its upper part, drive means 10, integral with its spindle 8, which impart a rotational movement to the mobile dispenser 6 via suitable intermediate means. In one of the embodiments of the invention as illustrated in FIGS. 1 and 2, the means 10 consist of a toothed wheel centered on the spindle of the drive unit, and the above-mentioned intermediate means consist of three toothed wheels 11 bearing against the wheel 10 in a symmetrical arrangement, separated by 120°, and cooperating with drive means 12 integral with the mobile dispenser 6, which in this case consist of a ring gear.

By appropriate dimensioning of the elements 10, 11 and 12 mentioned above, the torque can be uniformly distributed and the speed of rotation of the mobile dispenser 6 can be adapted to the values required by its function.

As indicated, the drive unit 4, which is not shown in detail, is coupled to a timer: it can be a customary mechanical, electrical (battery-powered) or electromechanical motor provided it can be adapted to the dimensions of the device. As has been seen, the mechanisms for driving the mobile dispenser 6, like those controlling the speed of rotation, can be conventional, as can the timer. The timer can also comprise an acoustic device for alerting the user when the treatment operations are complete, for example after a rotation of 360° or more, depending on the particular case.

According to the invention, the mobile dispenser 6 for dispensing unit doses of reagents is centered on the cover piece 3 and, as seen previously, bears on the said piece 3. In the embodiment illustrated in FIG. 1, the mobile dispenser is a hollow cylinder whose external diameter is identical or virtually identical to that of the base of the reservoir 1 and has at its center a housing 27 providing sufficient space for the drive unit 4. The ring gear 12 described previously is arranged in the upper part of the said housing 27. Near its periphery, the mobile dispenser 6 has inlet means 7 for separately bringing each of the unit doses of reagents opposite the orifice 5 in the piece 3: in this particular case, the said inlet means consist of several vertical channels 13 provided in the body of the cylinder, all of them being centered on the same circle and of course individually aligned with the orifice 5 when they are brought into the required position during the rotation of the mobile dispenser 6. Other arrangements can be designed provided they comply with the juxtaposition conditions defined above.

If desired, the device according to the invention can have reference marks displaying the respective positions of its fixed and mobile elements, in particular the positions of the inlet means 7 and the orifice 5 in the cover piece 3. For such purposes, appropriate marks or indicators can be placed on the outer surface of the mobile dispenser 6 and of the reservoir 1, for example, this type of reference mark making it possible easily to indicate a position in which the device is stopped or is functioning, or alternatively a position in which the doses are being charged or the immersed objects are being treated.

In one particular embodiment of the invention, the device has a lid 14 which is preferably fixed to the upper part of the unit 4, for example by means of studs 28 arranged symmetrically in alternation with the toothed wheels 11. In such an embodiment, the lid 14 has a hole 15 for easy access to the channels 13 (bounded by a dot-and-dash line in FIG. 2). In this way, the upper portion of each of the channels 13 can be exposed for introduction of the unit doses of reagents (charging phase) and subsequently covered once the mobile dispenser 6 has been caused to rotate (functioning phase).

Figure 4:
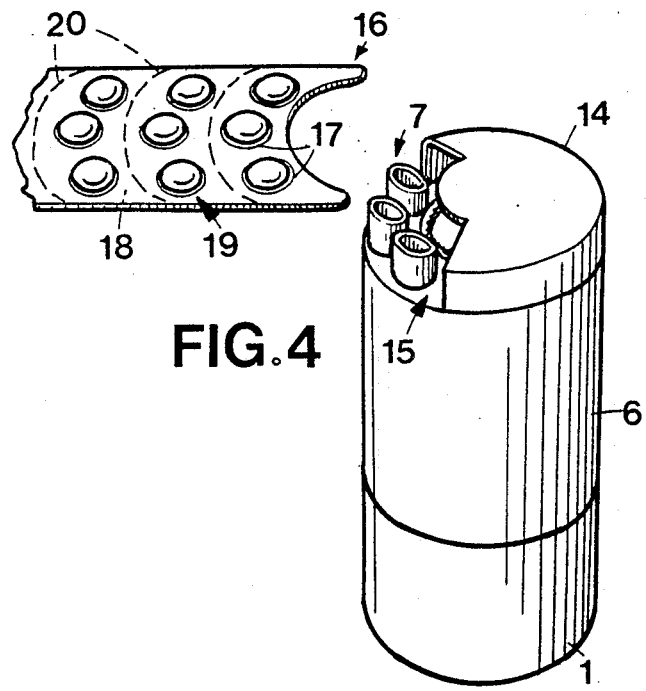
FIG. 4 shows a kit according to one embodiment of the invention.

As indicated, the invention further relates to a kit consisting of the device described above and a container 16 in which the unit doses of reagents are stored. One particular embodiment of such a kit is shown in FIG. 4.

According to the invention, the storage container 16 comprises one or more cells 17 acting as a receptacle for the unit doses of reagents, each of the cells 17 being closed by a tearable cover 18. Such a container can advantageously consist of an appropriately preformed sheet of polymeric material with the cells 17 projecting from one of its faces, an aluminum foil, for example, being welded or glued to the other face. A corresponding cover 18 is then outlined opposite each cell and can be torn simply by pushing the cell onto the channel 13.

In one particular embodiment of the kit according to the invention, the storage container 16 has several cells 17, each containing a single unit dose of reagent. In such a case, the cells 17 are arranged in groups 19 (for example groups of three) and each cell in the group 19 contains a unit dose of a different reagent. Moreover, each of the said groups 19 is separated from the next by a tear line 20. In this particular embodiment, the cells in the group are preferably arranged on an arc of a circle corresponding to that defined by the channels 13. This avoids any confusion regarding the assignment of the unit dose to a specific channel. Likewise, the tear line 20 will also be arranged in an arc of a circle.

To illustrate in greater detail how the objects of the invention are put into effect, the use of a device for the treatment of soft contact lenses will be described below. In such a case, the dimensions of the device are of the order of a few centimeters, the chosen embodiment corresponding to that shown in FIG. 1. In addition, the way in which this device functions is illustrated schematically by means of FIGS. 5A to 5D.

A suitable amount of sterile physiological saline (0.9% NaCl in $H_2O$) is placed in the reservoir 1 and the receptacle 2 containing the contact lenses is then immersed.

The cover piece 3, to which the receptacle 2 is fixed, is then screwed onto the reservoir. The arrangement of the constituent elements of the device is designed in such a way that the user holds in one hand the assembly formed by the cover piece 3 supporting the drive unit 4, the mobile dispenser 6 and the lid 14.

Once the cover piece 3 has reached the end of its travel, a rotational movement of about 360° or more, for example, is communicated to the mobile dispenser 6, which has the effect of rewinding the mechanism of the drive unit 4 if it is a spring mechanism. In the case of an electrical or electromechanical drive unit, this operation is not compulsory.

Figure 5A:
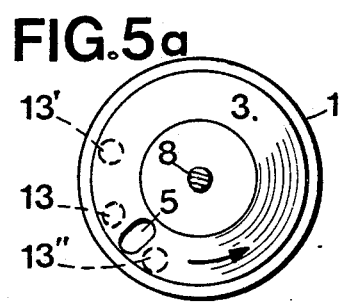
FIG. 5A, 5B, 5C and 5D are schematic views illustrating how one embodiment of the invention functions.
Figure 5B:
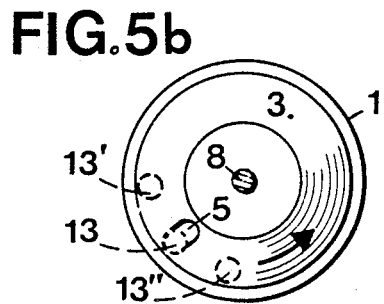
Figure 5C:
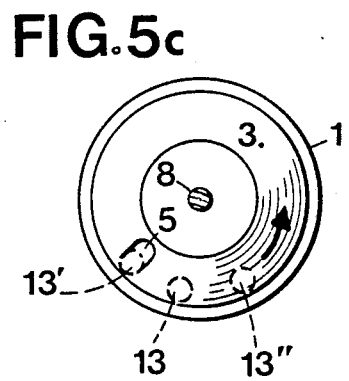
Figure 5D:
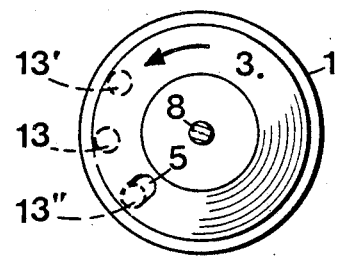

When the above-mentioned mechanism is ready to run, the arrangement of the device is as follows, the space between the three channels 13, 13' and 13'' being sufficient for their respective bases to be located on either side of the orifice 5: thus the base of the channel 13" is located downstream of the said orifice 5, in the direction of the rotation which is to be communicated to the mobile dispenser by the drive unit 4, the base of the channel 13 is then located upstream of the orifice 5 and the base of the channel 13' is upstream of that of the channel 13. Also according to this arrangement, the upper end of these same channels comes out into the hole 15, as illustrated in FIG. 4. A group 19 of unit doses from the storage container 16 is then placed over the upper end of the said channels 13, 13' and 13" and, after the cover has been pushed out, each of the prepared unit doses is introduced into its respective channel (charging phase). This arrangement is illustrated in FIG. 5A.

It is at this point that the user can start the drive unit 4, for example by releasing the winder mechanism. The rotation of the mobile dispenser then carries the unit dose placed in the channel 13 until it is opposite the orifice 5, ready for automatic transfer into the reservoir 1 (FIG. 5B): this first dose consists of a stable tablet of NaCl/NaClO$_2$. Continuing its rotation, the dispenser carries the unit dose placed in the channel 13' until it passes automatically into the reservoir 1 through the orifice 5 (FIG. 5C): this second dose consists of a tablet containing a sufficient amount of citric acid to maintain the desired pH within the liquid during the treatment. The dissolution of the first two doses introduced into the liquid in this way enables the oxidizing product to act at the optimum pH: this represents the phase in which the contact lenses are cleaned and decontaminated. Continuing its rotation, the mobile dispenser, after practically one complete revolution, reaches the position in which the channel 13" is aligned with the orifice 5 (FIG. 5D), resulting in automatic transfer of the third unit dose into the reservoir 1. This time the dose consists of a neutralizing tablet based on sodium perborate: the neutralization and stabilization phase can then start. The speed of rotation can be calculated so that the cleaning phase takes about 15 to 20 min. Once the period assigned to the neutralization phase is complete, an acoustic or visual signal alerts the user, who can then remove the receptacle from the reservoir and, if necessary, rinse the treated lenses with a further amount of sterile physiological saline. The contact lenses are then ready to use.

In another way of carrying out the treatment detailed above, the following reagents will be used:
first dose (oxidizing product): sodium dichloroisocyanurate
second dose (pH regulator): salts of the sodium phosphate or borate type
third dose (neutralizing product): sodium thiosulfate.

In another way of carrying out the said treatment, the procedure is different again: a suitable amount of 3% hydrogen peroxide in water (oxidizing product) is introduced into the container 1 in place of the above-mentioned physiological saline. In such a case, it will be necessary only to introduce the dose of reagent serving to regulate the pH, for example sodium chloride, followed by the dose of neutralizing product, for example sodium bisulfite or perborate.

The treatment described above is carried out daily; at longer intervals, for example weekly, the neutralization treatment can be complemented with an enzyme treatment for the purpose of "deproteinizing" the lenses. This is done simply by adding a dose of the appropriate enzyme product to the unit dose of neutralizing product, which will then be carried with the latter by the rotation of the mobile dispenser.

Of course, the other treatment variants explained above can also be carried out using the device.

The advantage of such devices is that they enable more concentrated reagents to be used, which are more powerful than those made available to the user hitherto, since the operations mentioned above are automated and perfectly time-controlled. A further result is that the period of treatment of the contact lenses is shortened accordingly.

Other embodiments of the device can obviously be envisaged, depending on the use for which it is intended, whether this be, for example, the cleaning of dental prostheses, the treatment of photographic films or chemical or biochemical reactions performed for analytical purposes. In such cases, the dimensions of the device of the invention can be substantially greater than those mentioned above, without thereby modifying the particular arrangement of its various constituent elements.

What is claimed is:

1. A device for the sequential treatment of immersed objects with dissolved reagents, comprising
   a reservoir (1) for containing a reagent solution,
   a receptacle (2) for keeping the objects to be treated immersed in the reservoir (1),
   a cover piece (3) fixed to a top of the reservoir (1), supporting at its center a drive unit coupled to a timer (4), said cover piece having near its periphery an orifice (5) for transferring unit doses of reagents into the reservoir (1), and
   a mobile dispenser (6) of unit doses of reagents which is centered on the cover piece (3) and bears on said cover piece (3), said dispenser being rotated by the drive unit (4), and having near its periphery inlet means (7) for separately bringing each of the unit doses of reagents opposite the orifice (5) in the cover piece (3).

2. The device according to claim 1, which has reference marks displaying respective positions of the inlet means (7) and the orifice (5) in the cover piece (3).

3. The device according to claim 1, which has a lid (14) fixed to an upper part of the drive unit (4), said lid having at its periphery a hole (15) for access to the inlet means (7).

4. The device according to claim 1, wherein the receptacle (2) is integral with the cover piece (3).

5. The device according to claim 1, wherein the receptacle (2) is integral with a spindle (8) of the drive unit (4) and is driven by said spindle as it rotates.

6. The device according to any one of claims 1 to 3, wherein the cover piece (3) is frustoconical and has at its top a housing (9) for receiving the drive unit (4), a base of the mobile dispenser (6) in contact with the cover piece (3) having a frustoconical shape mated to said cover piece.

7. The device according to claim 1 wherein the drive unit (4) has at its upper part a first drive means (10) integral with a spindle (8) and transmission, means (11) cooperating with a second, drive means (12), said second drive means being integral with the mobile dispenser (6).

8. The device according to claim 7, wherein the first drive means (10) and transmission means (11) are toothed wheels and the second drive means (12) (6) consist of a ring gear.

9. The device according to claim 1 wherein the inlet means (7) consist of one or more channels (13) provided in the mobile dispenser (6), near its periphery.

10. The device according to claim 9, wherein the mobile dispenser (6) has a cylindrical external shape and the inlet means (7) consist of one or more vertical channels (13).

11. A kit consisting of the device according to claim 1 and a container (16) in which unit doses of reagents are stored.

12. The kit according to claim 11, wherein the container (16) comprises one or more cells (17) acting as a receptacle for the unit doses of reagents, each of the cells (17) being closed by a tearable cover (18).

13. The kit according to claim 12, wherein the container (16) has several cells (17) arranged in groups (19), each of the cells in containing a single unit dose of a different reagent.

14. The kit according to claim 13, wherein each of said groups (19) is separable from other of said groups by a tear line (20).

* * * * *